United States Patent
Ohara et al.

(10) Patent No.: US 8,647,845 B2
(45) Date of Patent: Feb. 11, 2014

(54) METHOD FOR PRODUCING SUGAR

(71) Applicants: Asahi Group Holdings, Ltd., Tokyo (JP); Incorporated Administrative Agency National Agriculture and Food Research Organization, Tsukuba (JP)

(72) Inventors: Satoshi Ohara, Moriya (JP); Yoshifumi Terajima, Nishinoomote (JP); Akira Sugimoto, Ishigaki (JP)

(73) Assignees: Asahi Group Holdings, Ltd., Tokyo (JP); Incorporated Administrative Agency National Agriculture and Food Research Organization, Tsukuba-shi (JP)

(*) Notice: Subject to any disclaimer, the term of this patent is extended or adjusted under 35 U.S.C. 154(b) by 0 days.

(21) Appl. No.: 13/785,860

(22) Filed: Mar. 5, 2013

(65) Prior Publication Data

US 2013/0183724 A1     Jul. 18, 2013

Related U.S. Application Data

(63) Continuation of application No. 13/063,044, filed as application No. PCT/JP2009/066092 on Sep. 15, 2009.

(30) Foreign Application Priority Data

Sep. 16, 2008   (JP) .................................. 2008-236727

(51) Int. Cl.
*C12P 19/12* (2006.01)
(52) U.S. Cl.
USPC ........................................................ 435/100
(58) Field of Classification Search
USPC ........................................................ 435/100
See application file for complete search history.

(56) References Cited

U.S. PATENT DOCUMENTS

| | | | |
|---|---|---|---|
| 4,335,207 A * | 6/1982 | Heady | ............................ 435/94 |
| 4,978,539 A | 12/1990 | Colin et al. | |
| 7,575,640 B2 | 8/2009 | Pollach | |
| 2006/0035355 A1 | 2/2006 | Ohara et al. | |

FOREIGN PATENT DOCUMENTS

| | | |
|---|---|---|
| CN | 1802441 A | 7/2006 |
| JP | 2004-321174 A | 11/2004 |
| SU | 1838397 A3 | 8/1993 |
| WO | WO-2004/081236 A1 | 9/2004 |
| WO | WO-2008/002445 A3 | 5/2008 |

OTHER PUBLICATIONS

Ohara et al., "Biomass Ethanol Production from Sugarcane for Engery Generation to Support Sugar Prodution," *Journal of the Japan Institute of Energy*, 84:923-928 (2005).
Ohara et al., "Simultaneous Production of Sugar and Ethanol from Hign-Biomass Sugarcane in Japan," *Bio Industry*, 24:7-14 (2007).
International Search Report for Application No. PCT/JP2009/066092, dated Oct. 13, 2009.
Decision of Granting a Patent for Invention for Russian Application No. 2011115062/10(022339), dated Oct. 3, 2012.

* cited by examiner

*Primary Examiner* — D. Lawrence Tarazano
*Assistant Examiner* — Hamid R Badr
(74) *Attorney, Agent, or Firm* — Marshall, Gerstein & Borun LLP

(57) ABSTRACT

Provided is a method for efficiently producing sugar and simultaneously efficiently producing ethanol. A method for producing sugar characterized by comprising a pretreatment step in which a plant-origin sugar solution is fermented by a microorganism having no sucrose-degrading enzyme and a step for producing sugar from the fermented sugar solution. A method for producing sugar characterized by comprising a pretreatment step in which a plant-origin sugar solution is fermented by a microorganism in the presence of a sucrose-degrading enzyme inhibitor and a step for producing sugar from the fermented sugar solution.

4 Claims, 6 Drawing Sheets

FIG.5
○ EXAMPLE OF FERMENTATION OF PRESSED JUICE IN CASE USING GENERAL YEAST (CONTROL PLOT)
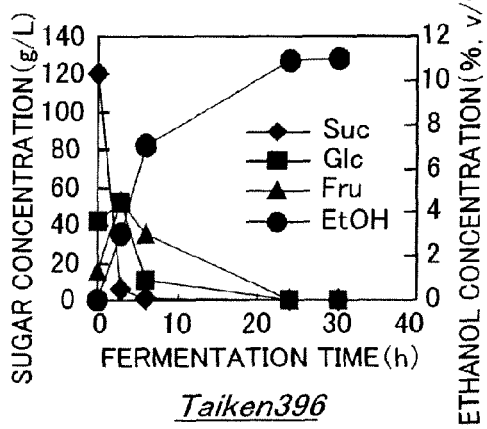
Taiken396
○ EXAMPLE OF FERMENTATION OF PRESSED JUICE IN CASE USING YEAST HAVING SUCRASE GENE DISRUPTED
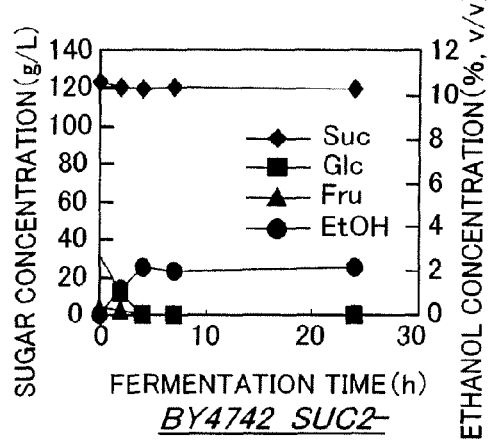
BY4742 SUC2−
○ EXAMPLES OF FERMENTATION OF PRESSED JUICE IN CASE USING YEAST HAVING NO SUCRASE (FOUR STRAINS)
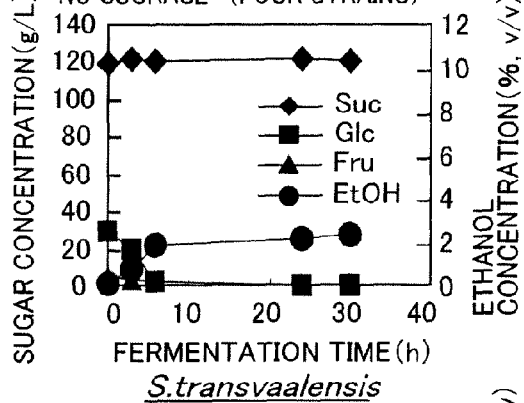
S.transvaalensis
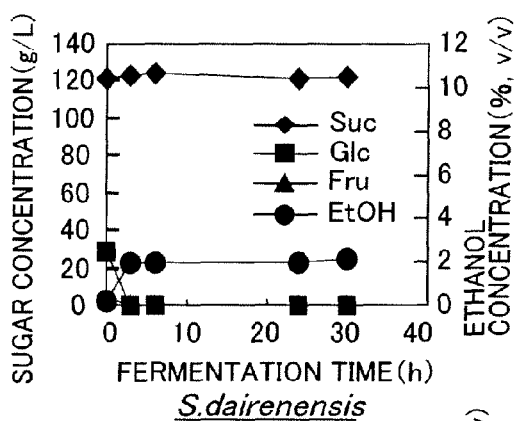
S.dairenensis
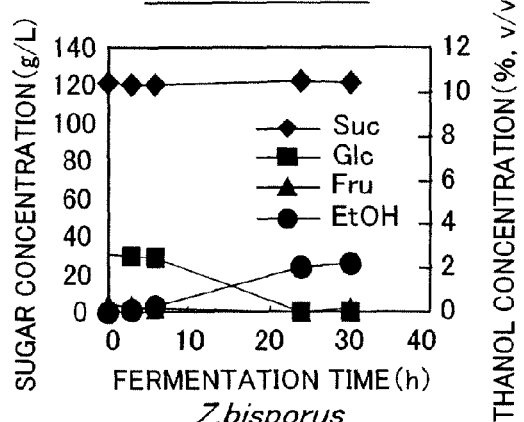
Z.bisporus
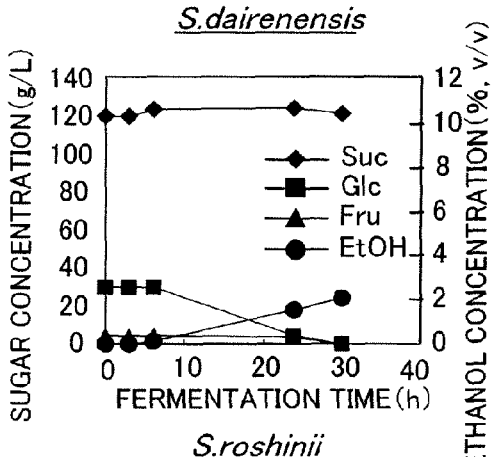
S.roshinii

FIG.6
○ EXAMPLE OF FERMENTATION OF PRESSED JUICE IN CASE USING GENERAL YEAST (WITHOUT INHIBITOR) (CONTROL PLOT)
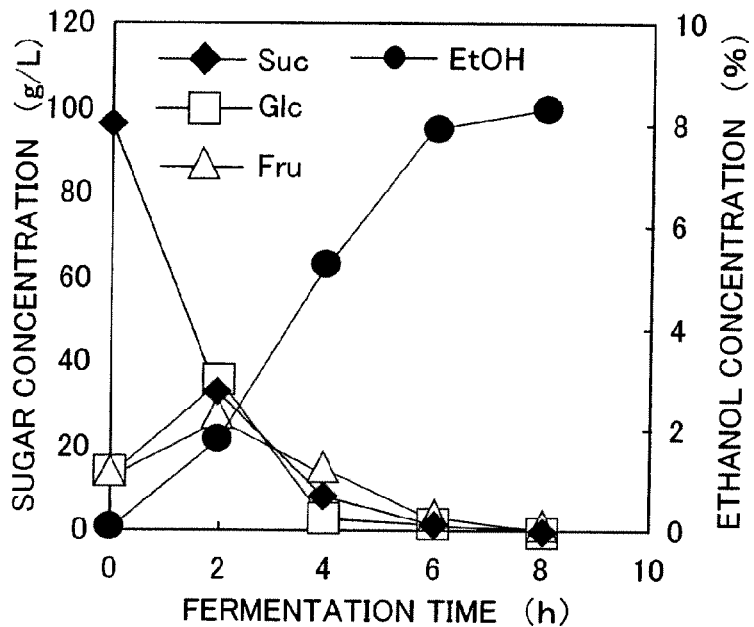
○ EXAMPLE OF FERMENTATION OF PRESSED JUICE IN CASE USING GENERAL YEAST (WITH INHIBITOR)
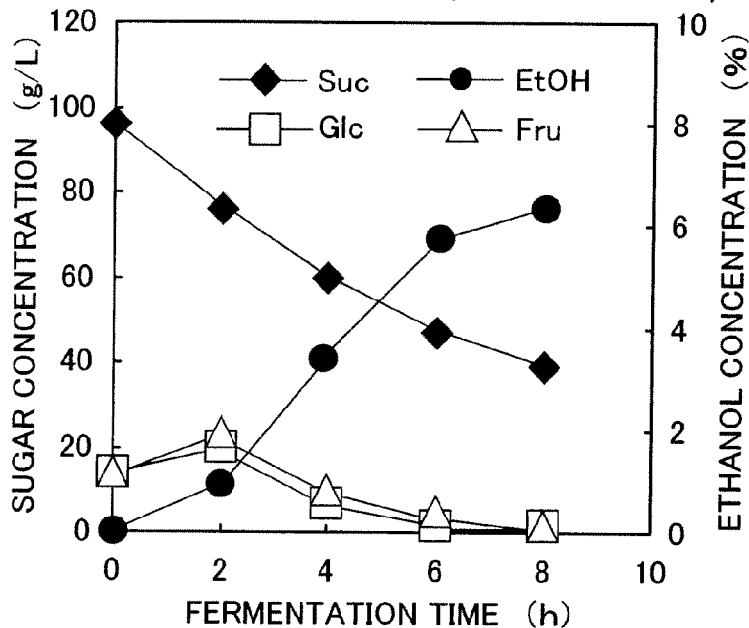

METHOD FOR PRODUCING SUGAR

CROSS REFERENCE TO RELATED APPLICATIONS

This is a continuation of U.S. Ser. No. 13/063,044 filed Mar. 9, 2011, which is the U.S. national phase of PCT/JP2009/066092 filed Sep. 15, 2009, based on JP 2008-236726 filed Sep. 16, 2008, the entire respective disclosures of which are incorporated herein by reference.

TECHNICAL FIELD

The present invention relates to a sugar production method, and more specifically relates to a method for efficiently producing sugar and ethanol.

BACKGROUND ART

Ethanol fuel derived from plants is expected to be liquid fuel alternative to gasoline to prevent increase in carbon dioxide gas. When both sugar and ethanol are produced from a sugar juice derived from a plant, the following method has been employed. Specifically, first, sugar is produced from a sugar juice. The sugar juice after the sugar production is fermented by using a microorganism to produce ethanol (see, for example, JP-A 2004-321174).

SUMMARY OF THE INVENTION

Problems to be Solved by the Invention

In the above-described method, a crystallization process is needed to produce sugar from a sugar juice. For the crystallization process, the sugar concentration needs to be high. For this reason, it has been practiced that the sugar juice is heated to evaporate the water content and thereby is concentrated. Meanwhile, the high sugar concentration and the salinity in the sugar juice thus increased by heating and concentrating act as the inhibitory factor for the fermentation. Accordingly, a treatment such as dilution needs to be performed to produce ethanol from molasses after the sugar production. In addition, the above method is very ineffective in terms of energy, because the fermented liquid is heated again to extract the ethanol by distillation. Moreover, the sugar crystallization process has a problem such as reduction in a yield of sugar crystals, unless it uses a sugar juice with a high sucrose ratio, in other words, a sugar juice in which the content of a sucrose as a raw material of sugar is high relative to the total sugar amount including sugars that are other than the sucrose, and are not raw materials of the sugar. Accordingly, there is a problem that sugar cannot be produced, for example, in a period or from a cultivar having a low sucrose ratio.

An object of the present invention is to provide a method for efficiently producing sugar and efficiently producing ethanol simultaneously.

Means for Solving the Problems

The present invention provides a sugar production method characterized by including: a pretreatment step of fermenting a sugar juice derived from a plant by using a microorganism not having sucrase; and a step of producing sugar from the fermented sugar juice. In addition, the present invention provides a sugar production method characterized by including: a pretreatment step of fermenting a sugar juice derived from a plant by using a microorganism in the presence of a sucrase inhibitor; and a step of producing sugar from the fermented sugar juice.

Effects of the Invention

In the methods of the present invention, a sugar juice that is low in both sugar concentration and salinity is fermented. Thus, it is possible to efficiently produce ethanol.

BRIEF DESCRIPTION OF THE DRAWINGS

FIG. 5 shows graphs for a result of a fermentation test on sugarcane-pressed juices using yeasts not having sucrase and a yeast having a sucrase gene disrupted.
FIG. 6 shows graphs for a result of a fermentation test on sugarcane-pressed juices using a sucrase inhibitor.

MODES FOR CARRYING OUT THE INVENTION

Figure 1:
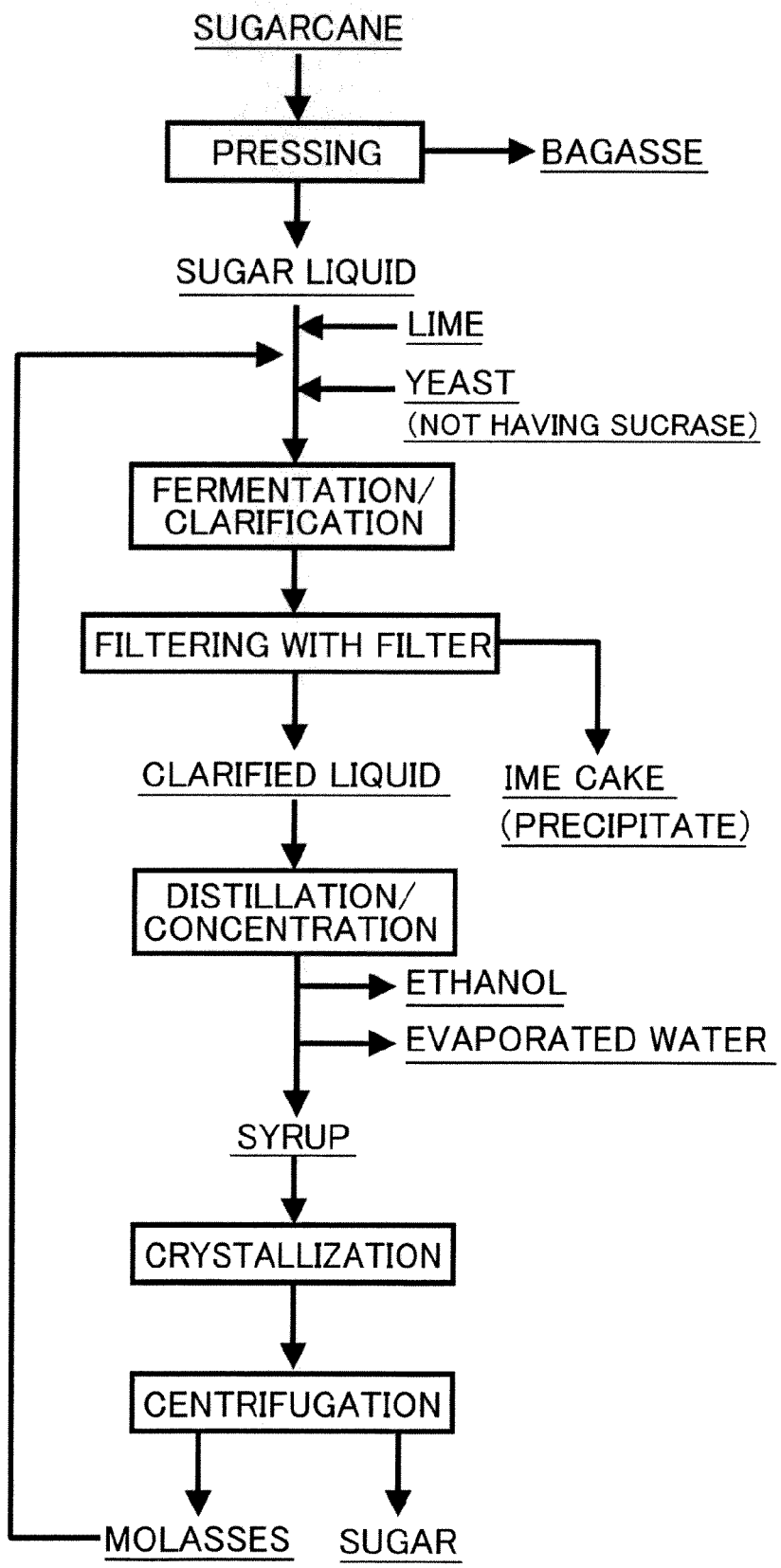
FIG. 1 is a flowchart of a process used in Example 1.

A sugar production method of the present invention includes a pretreatment step of fermenting a sugar juice from a plant by using a microorganism not having sucrase, or a pretreatment step of fermenting a sugar juice derived from a plant by using a microorganism in the presence of a sucrase inhibitor. Since the sugar juice is fermented under such a condition, sucrose is not decomposed, but ethanol and so forth are produced only from invert sugars such as glucose and fructose. As a result, the proportion of sucrose in the sugar juice is increased, and thus the efficiency of crystallizing sugar can be improved. Meanwhile, the conventional method has a problem of difficulty in crystallizing raw materials which have high sugars other than sucrose and which have low sucrose ratios (due to the cultivar and the harvesting period). However, in the sugar production method of the present invention, the sugars other than sucrose are consumed by the fermentation, thus increasing the sucrose ratio. Accordingly, even raw materials having low sucrose ratios can be crystallized. This leads to increase in the utilizable range of sugarcane cultivars and extension in the harvesting period. Additionally, in the conventional method, nitrogen and the sugars combine with each other during the sugar production, coloring the molasses. This causes a problem of coloring exhaust water. However, in the sugar production method of the present invention, nitrogen is consumed by the fermentation, thus reducing the coloring of molasses. Furthermore, in the conventional method, the production period is long (approximately 48 to 72 hours) because all of the high-concentration sugar after the sugar production has to be converted into ethanol. The fermentation is also inhibited by the salt concentration. However, in the sugar production method of the present invention, the low-concentration sugar is fermented. Accordingly, the fermentation is completed in a short period of time with less salt concentration. Thus, the production period can be shortened greatly.

Examples of the plant include plants that accumulate sugars such as sugarcane and sugar beet. Sugarcane is preferable.

A step of preparing the sugar juice derived from the plant can be accomplished by methods known to those skilled in the art, for example, a pressing step. Specifically, cane stem portions of reaped sugarcane are cut into pieces of 15 to 30 cm length with a cutter, and finely shredded with a shredder. The sugar juice is squeezed out with a roll mill. To improve the efficiency of squeezing out the sugars, water is poured into an end roll, and 95 to 97% of the sugars are squeezed out. Then, in a lime mixing bath, lime is added to the juice. After impurities aggregate and precipitate, the precipitate and the clarified liquid are separated from each other with an oliver filter. The clarified liquid is concentrated by evaporation. The obtained sugar juice mainly contains sucrose, glucose, fructose, and so on.

Examples of the microorganism not having sucrase include Saccharomyces dairenensis NBRC 0211, Saccharomyces transvaalensis NBRC 1625, Saccharomyces rosinii NBRC 10008, Zygosaccharomyces bisporus NBRC 1131, and the like. Meanwhile, among the microorganisms having sucrase, it is possible to use a fungal strain of microorganisms whose six sucrase genes (SUC1, SUC2, SUC3, SUC4, SUC6, SUC7) are all or partially disrupted by genetic engineering.

Examples of the sucrase inhibitor include a silver ion, copper ion, mercury ion, lead ion, methyl-α-D-glucopyranoside, PCMB (p-chloromercuribenzoate), glucosyl-D-psicose, and the like.

The fermentation can be carried out by methods known to those skilled in the art. Examples thereof includes a batch method in which a fermentable microorganism and a sugar juice are blended at a predetermined ratio for fermentation, a continuous method in which a fermentable microorganism is immobilized and then supplied with a sugar juice continuously for fermentation, and the like.

The sugar production method of the present invention subsequently includes a step of producing sugar from the fermented sugar juice. The sugar can be produced from the fermented sugar juice by methods known to those skilled in the art. Examples thereof include crystallization of sugar, and the like. Specifically, the fermented sugar juice is repeatedly heated and concentrated little by little (0.5 to 1 kl) under reduced pressure by suction. Sugar crystals of a certain size or larger is taken out. Then, the sugar crystals and the sugar juice are separated from each other with a centrifuge.

The sugar production method of the present invention may include a step of collecting ethanol from the fermented sugar juice before the sugar is produced from the fermented sugar juice. The ethanol can be collected from the fermented sugar juice by methods known to those skilled in the art. An example includes separation of the ethanol through distillation. If the ethanol is separated through the distillation, the sugar juice is concentrated simultaneously. Thus, it is no longer necessary to perform the heating and concentrating again in the sugar production. Hence, both of time and energy can be saved.

EXAMPLES

Example 1

Process Verification for Case of Using Sugarcane as Raw Material and Yeast not having Sucrase (1) Pressing Step Cane stem portions, weighing 3200 g, of a sugarcane (NiF8) after harvest were shredded with a shredder, and then pressed with a four-roll mill. Thereby, 3114 mL of a pressed juice was obtained (pressed juice weight=3348 g, sucrose content=563 g, invert sugar content=65 g, sucrose ratio=79.4%).

(2) Clarification/Fermentation Steps

The pressed juice was transferred to a 5-L jar fermentor, and hydrated lime Ca(OH)2 of 0.05% by weight relative to the weight of the pressed juice was added thereto for the pH adjustment and aggregation of impurities. Then, 0.3 g in dry weight of yeast Saccharomyces dairenensis (NBRC 0211) not having sucrase was planted therein for ethanol fermentation under anaerobic conditions at 30° C. for 3 hours. The yeast precultured in advance in a YM medium was used. After the fermentation was completed, the yeast and the aggregated impurities were filtered through a filter. Thereby, separated was a fermented liquid of 3080 mL (pressed juice weight=3288 g, ethanol concentration of 1.17 vol %, sucrose content=558 g, invert sugar content=0 g).

(3) Ethanol Distillating/Sugar Juice Concentrating Steps

The fermented liquid was heated under reduced pressure, and 28.6 g of ethanol thus evaporated was cooled and collected. Then, 2193 mL of water was successively evaporated. Thereby, 837 mL of a concentrated sugar juice was obtained (sugar juice weight=1066 g, sucrose content=558 g, invert sugar content=0 g, sucrose ratio=93.8%).

(4) Crystallization Step

Half of the sugar juice was extracted, which was further heated under reduced pressure and concentrated until the supersaturation for the sucrose reached 1.2. Then, 50 g of a seed crystal (particle size of 250 μm) for the sugar was added, and a crystal was formed in approximately 3 hours while the rest of the concentrated sugar juice was added little by little.

(5) Raw Sugar/Molasses Separation Step

The mixture of the crystallized sugar and the molasses was centrifuged in a perforated wall type centrifuge using a filter cloth of 50- to 100-μm mesh at 3000 rpm for 20 minutes. Thereby, 371 g of the sugar (sucrose collecting rate=65.9%: excluding the added seed crystal) and 234 g of the molasses (sucrose content=151 g, invert sugar content=0 g, sucrose ratio=87.4%) were separated from each other.

Figure 2:
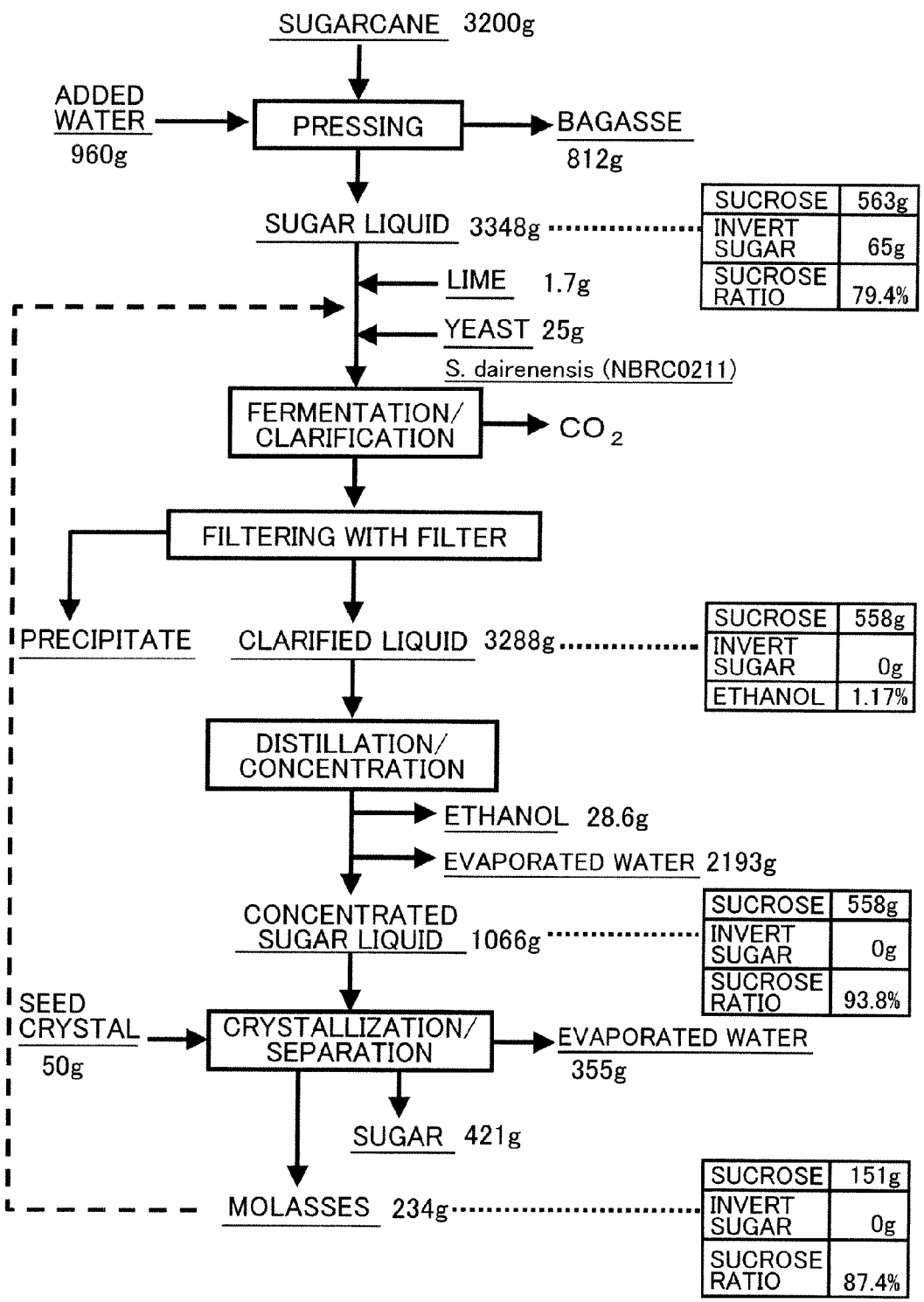
FIG. 2 is a chart illustrating the mass balance in the process of Example 1.

FIG. 1 shows a flowchart of the production process, and FIG. 2 shows the result of the mass balance.

Example 2

Process Verification for Case of Using Sugarcane as Raw Material and Sucrase-Gene-Disrupted Strain (1) Pressing Step Cane stem portions, weighing 3200 g, of a sugarcane (NiF8) after harvest were shredded with a shredder, and then pressed with a four-roll mill. Thereby, 3000 mL of a pressed juice was obtained (pressed juice weight=3264 g, sucrose content=546 g, invert sugar content=60 g, sucrose ratio=78.9%).

(2) Clarification/Fermentation Steps

The pressed juice was transferred to a 5-L jar fermentor, and hydrated lime $Ca(OH)_2$ of 0.05% by weight relative to the weight of the pressed juice was added thereto for the pH adjustment and aggregation of impurities. Then, 0.3 g in dry weight of yeast strain Saccharomyces cervisiae BY4742 whose sucrase gene SUC2 was disrupted was planted therein for ethanol fermentation under anaerobic conditions at 30° C. for 3 hours. The disrupted strain precultured in advance in a YM medium was used. After the fermentation was completed, the yeast and the aggregated impurities were filtered through a filter. Thereby, separated was a fermented liquid of 2986 mL (pressed juice weight=3180 g, ethanol concentration of 1.38 vol %, sucrose content=546 g, invert sugar content=0 g).

(3) Ethanol Distillating/Sugar Juice Concentrating Steps

The fermented liquid was heated under reduced pressure, and 32.8 g of ethanol thus evaporated was cooled and collected. Then, 2083 mL of water was successively evaporated. Thereby, 860 mL of a concentrated sugar juice was obtained (sugar juice weight=1065 g, sucrose content=546 g, invert sugar content=0 g, sucrose ratio=87.1%).

(4) Crystallization Step

Half of the sugar juice was extracted, which was further heated under reduced pressure and concentrated until the supersaturation for the sucrose reached 1.2. Then, 50 g of a seed crystal (particle size of 250 μm) for the sugar was added, and a crystal was formed in approximately 3 hours while the rest of the concentrated sugar juice was added little by little.

(5) Raw Sugar/Molasses Separation Step

The mixture of the crystallized sugar and the molasses was centrifuged in a perforated wall type centrifuge using a filter cloth of 50- to 100-μm mesh at 3000 rpm for 20 minutes. Thereby, 351 g of the sugar (sucrose collecting rate=64.3%: excluding the added seed crystal) and 239 g of the molasses (sucrose content=123 g, invert sugar content=23 g, sucrose ratio=65.8%) were separated from each other.

Figure 3:
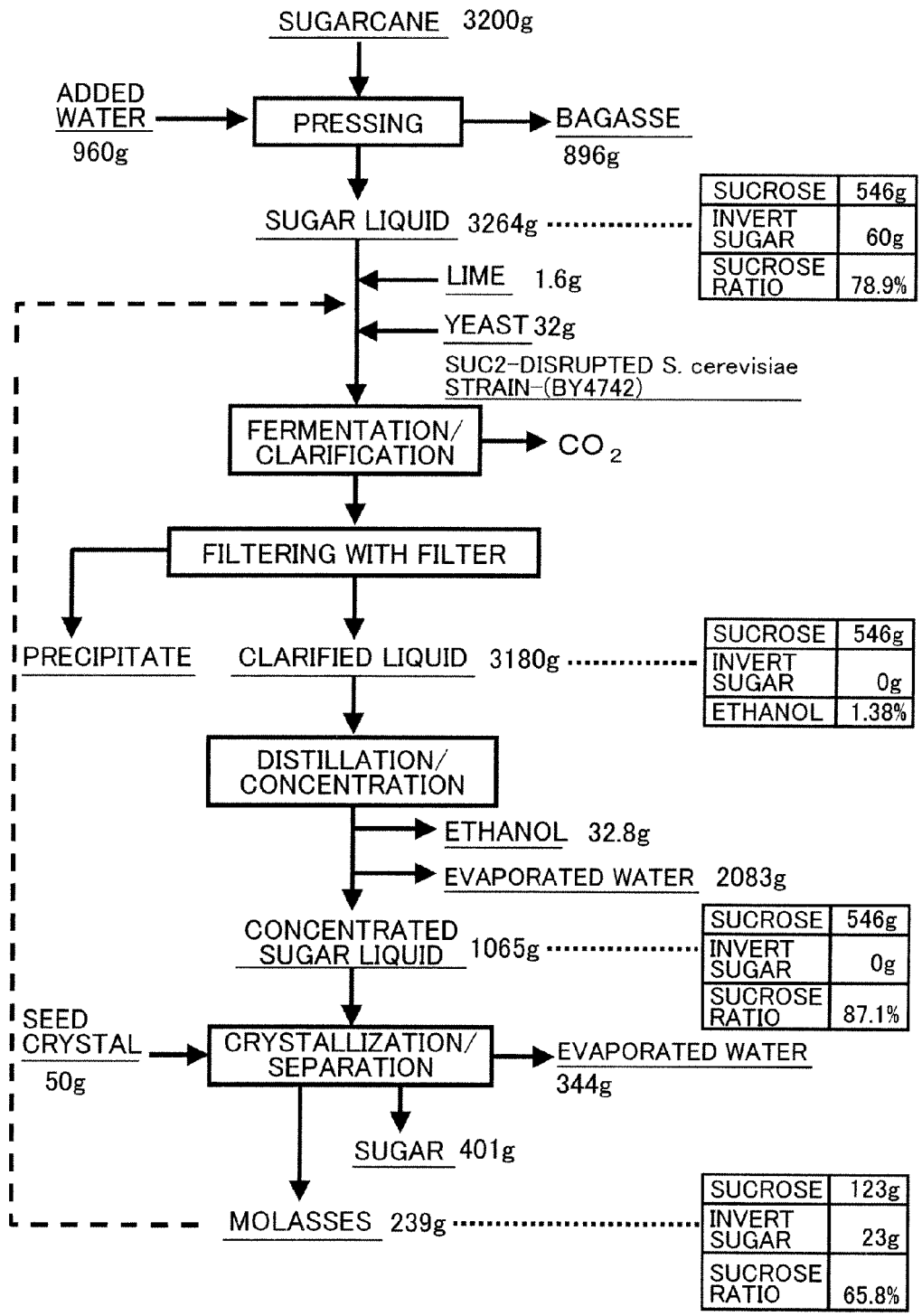
FIG. 3 is a chart illustrating the mass balance in a process of Example 2.

FIG. 3 shows the result of the mass balance.

Example 3

Process Verification for Case of Using Sugarcane as Raw Material and Sucrase Inhibitor (1) Pressing Step Cane stem portions, weighing 3000 g, of a sugarcane (NiF8) after harvest were shredded with a shredder, and then pressed with a four-roll mill. Thereby, 2868 mL of a pressed juice was obtained (pressed juice weight=3120 g, sucrose content=524 g, invert sugar content=61 g, sucrose ratio=78.3%).

(2) Clarification/Fermentation Steps

The pressed juice was transferred to a 5-L jar fermentor, and hydrated lime $Ca(OH)_2$ of 0.05% by weight relative to the weight of the pressed juice was added thereto for the pH adjustment and aggregation of impurities. After methyl-α-D-glucopyranoside serving as a sucrase inhibitor was added thereto at a concentration of 60 mM, 0.6 g in dry weight of yeast Saccharomyces cervisiae (Taiken 396 strain) having sucrase was planted therein for ethanol fermentation under anaerobic conditions at 30° C. for 6 hours. The yeast precultured in advance in a YM medium was used. After the fermentation was completed, the yeast and the aggregated impurities were filtered through a filter. Thereby, separated was a fermented liquid of 2870 mL (pressed juice weight=3064 g, ethanol concentration of 6.20 vol %, sucrose content=252 g, invert sugar content=0 g).

(3) Ethanol Distillating/Sugar Juice Concentrating Steps

The fermented liquid was heated under reduced pressure, and 150 g of ethanol thus evaporated was cooled and collected. Then, 2494 mL of water was successively evaporated. Thereby, 330 mL of a concentrated sugar juice was obtained (sugar juice weight=420 g, sucrose content=252 g, invert sugar content=0 g, ratio=94.0%).

(4) Crystallization Step

Half of the sugar juice was extracted, which was further heated under reduced pressure and concentrated until the supersaturation for the sucrose reached 1.2. Then, 50 g of a seed crystal (particle size of 250 μm) for the sugar was added, and a crystal was formed in approximately 3 hours while the rest of the concentrated sugar juice was added little by little.

(5) Raw Sugar/Molasses Separation Step

The mixture of the crystallized sugar and the molasses was centrifuged in a perforated wall type centrifuge using a filter cloth of 50- to 100-μm mesh at 3000 rpm for 20 minutes. Thereby, 203 g of the sugar (sucrose collecting rate=29.2%: excluding the added seed crystal) and 151 g of the molasses (sucrose content=88 g, invert sugar content=0 g, sucrose ratio=81.0%) were separated from each other.

Figure 4:
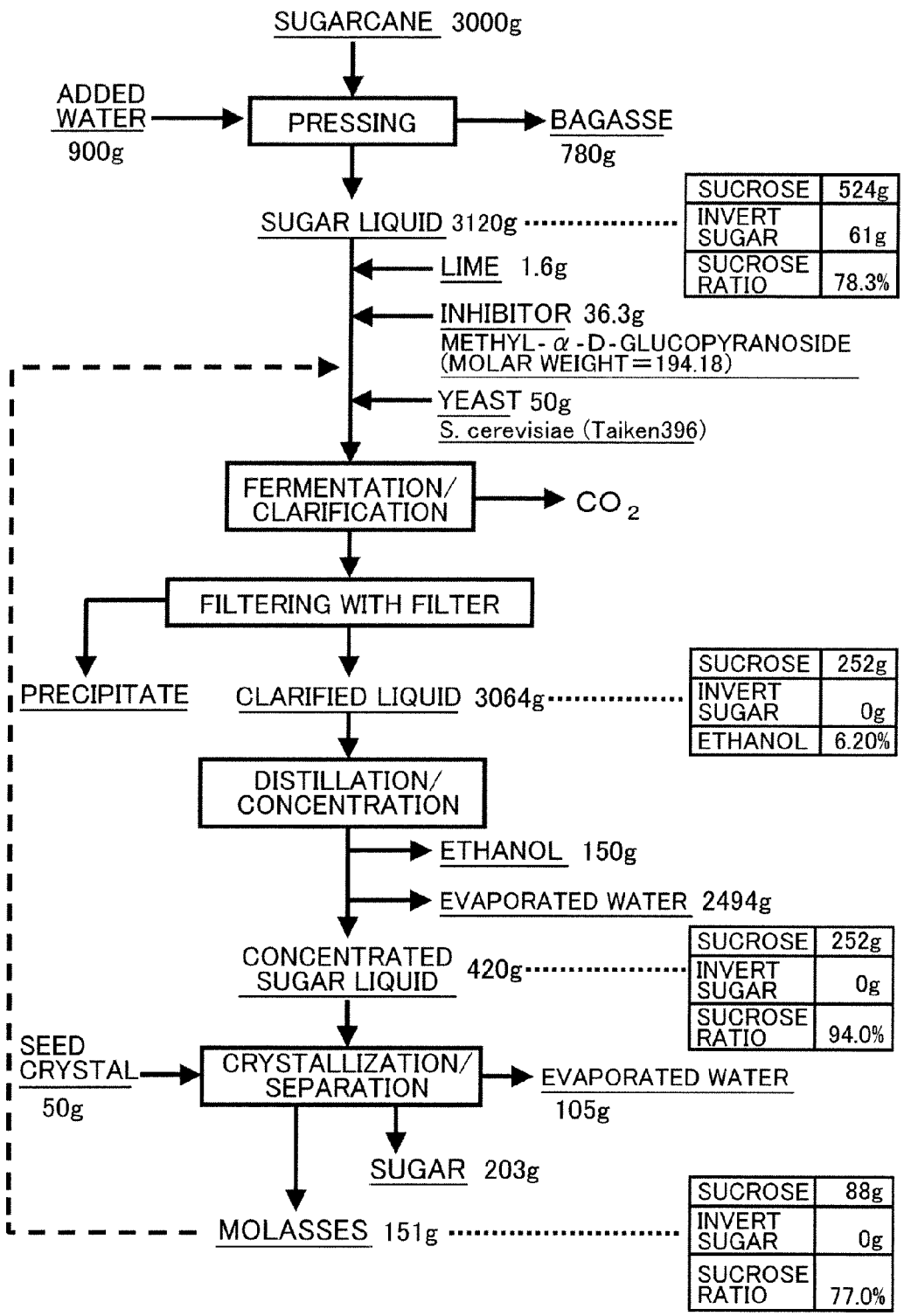
FIG. 4 is a chart illustrating the mass balance in a process of Example 3.

FIG. 4 shows the result of the mass balance.

Example 4

Fermentation Test on Sugarcane-Pressed Juice for Case of Using Yeast not having Sucrase S. dairenensis (NBRC 0211), S. transvaalensis (NBRC 1625), S. rosinii (NBRC 10008), Z. bisporus (NBRC 1131), which are yeasts not having sucrase and a strain (BY4742 SUC2-) of a yeast S. cervisiae BY4742 having sucrase gene disrupted were planted in a sugarcane-pressed juice. A fermentation test was conducted to confirm whether the sucrose was not decomposed and only the invert sugars were converted into ethanol. As reference for the comparison, a similar fermentation test was conducted using a yeast S. cervisiae (Taiken 396 strain) having sucrase.

Each of the fungal strains used for fermentation had been pre-precultured by shaking in 5 mL of a YM medium at 30° C. for 24 hours, and then further precultured by shaking in 300 mL of a YPD medium at 30° C. for 12 hours. The yeast was collected from the precultured medium by centrifugation. The yeast was suspended for fermentation in 100 mL of the pressed juice (in the pressed juice, the sucrose concentration was 12.0%, and the invert sugar concentration was 3.0%) placed in a 300-mL Erlenmeyer flask with a fermentation lock. The fermentation was carried out by shaking at 30° C. at 120 rpm. FIG. 5 shows the examined result of the changes in the sugar concentration and the ethanol concentration due to the fermentation over time.

For S. cervisiae (Taiken 396 strain) which is an ordinary yeast, due to the action of the sucrase, almost all of sucrose was decomposed into the invert sugars in 3 hours after the fermentation was started. In 24 hours, all of the sugars were converted into ethanol.

Meanwhile, for the four yeasts not having sucrase and the strain having the sucrase gene disrupted, although the ethanol synthesis speed varied among one another, sucrose decomposition was observed in none of the cases, and it was confirmed that only the invert sugars were converted into ethanol.

Example 5

Fermentation Test on Sugarcane-Pressed Juice for Case of Using Sucrase Inhibitor S. cervisiae (Taiken 396 strain) which is a general yeast having sucrase was planted in a sugarcane-pressed juice. Methyl-α-D-glucopyranoside serving as a sucrase inhibitor was added thereto at a concentration 60 mM. A fermentation test was conducted to examine the changes in the concentrations of sucrose, invert sugars, and ethanol over time.

The fungal strain used for fermentation had been pre-precultured by shaking in 10 mL of a YM medium at 30° C. for 24 hours, and then further precultured by shaking in 500 mL of a YPD medium at 30° C. for 12 hours. The yeast was collected from the precultured medium by centrifugation. 100 mL of the pressed juice (in the pressed juice, the sucrose concentration was 10.0%, and the invert sugar concentration was 3.0%) and 60 mM of methyl-α-D-glucopyranoside were placed in a 300-mL Erlenmeyer flask with a fermentation lock. The yeast collected from the precultured medium by centrifugation was added into the flask for fermentation. The fermentation was carried out by shaking at 30° C. at 120 rpm. FIG. 6 shows the examined result of the changes in the sugar concentration and the ethanol concentration due to the fermentation over time.

For *S. cervisiae* (Taiken 396 strain) which is an ordinary yeast, in a condition where no sucrase inhibitor exists, due to the action of the sucrase, almost all of sucrose was decomposed into the invert sugars in 6 hours after the fermentation was started, and then converted into ethanol. Since the sucrose decomposition speed was faster than the invert sugar-consumption speed of the yeast, the sucrose was completely consumed by the time when the invert sugars were consumed to thereby increase the sucrose ratio. It was accordingly confirmed that production of sugar from the fermented liquid was impossible.

Meanwhile, under the condition where the inhibitor existed, the sucrose decomposition speed was made slow, and approximately half of the sucrose remained in 6 hours after the fermentation was started, while all the invert sugars were converted into ethanol. The sucrose ratio of the fermented liquid was as high as 94.0% in 8 hours after the fermentation was started. The sucrose ratio of the fermented liquid would allow the crystallization of the sugar readily.

The invention claimed is:

1. A method for producing sucrose, the method comprising:
    extracting a sucrose-, fructose-, and glucose-containing juice from a plant containing said sucrose, fructose, and glucose;
    fermenting said juice using a microorganism having no sucrase or a microorganism having a disrupted sucrase gene whereby glucose and fructose are broken down to ethanol and sucrose is not broken down; and
    producing sucrose from the fermented juice.

2. The method according to claim 1, further comprising collecting ethanol from the fermented juice before the sucrose is produced from the fermented juice.

3. The method according to claim 2, wherein collecting the ethanol from the fermented juice includes separating the ethanol through distillation.

4. The method according to claim 1, wherein the plant is sugarcane.

* * * * *